United States Patent
Puckett et al.

(10) Patent No.: US 6,925,874 B2
(45) Date of Patent: Aug. 9, 2005

(54) APPARATUS FOR MEASURING THE RELATIVE DIFFICULTY IN DONNING A GLOVE

(75) Inventors: Nancy H. Puckett, Roswell, GA (US); Timothy Wilson Reader, Suwanee, GA (US); Wade R. Thompson, Cumming, GA (US); Thomas Gregory Triebes, Alpharetta, GA (US); Audra S. Wright, Woodstock, GA (US); Mark T. Pamperin, Cumming, GA (US); Joel Brostin, Alpharetta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 10/608,164

(22) Filed: Jun. 26, 2003

(65) Prior Publication Data

US 2004/0261527 A1 Dec. 30, 2004

(51) Int. Cl.$^7$ ................................................. A61B 1/24
(52) U.S. Cl. ................................................. 73/379.02
(58) Field of Search .......................... 73/379.01, 379.02, 73/379.03, 379.04, 832, 824, 826, 827; 223/111, 120, 112, 113

(56) References Cited

U.S. PATENT DOCUMENTS

| | | | | |
|---|---|---|---|---|
| 4,002,276 A | * | 1/1977 | Poncy et al. | 223/111 |
| 6,325,768 B1 | * | 12/2001 | Williams et al. | 600/595 |
| 6,419,131 B1 | * | 7/2002 | Rix | 223/111 |
| 6,427,883 B1 | * | 8/2002 | Esten | 223/111 |
| 6,497,340 B2 | * | 12/2002 | Grinberg | 221/45 |
| 6,578,433 B1 | * | 6/2003 | Yakopson et al. | 73/832 |
| 6,708,346 B2 | * | 3/2004 | Terris et al. | 2/161.2 |

OTHER PUBLICATIONS

Fisher, Mark D. et al., "Ease of Donning Commercially Available Powder–Free Surgical Gloves", *Journal of Biomedical Research*, vol. 33, 1996, pp. 291–295.

Fisher, Mark D. et al., "Biochemical Performance of Latex and Non–Latex Double–Glove Systems", University of Virginia School of Medicine, Jul. 1999, pp. 797–806.

* cited by examiner

*Primary Examiner*—Edward Lefkowitz
*Assistant Examiner*—Jewel V. Thompson
(74) *Attorney, Agent, or Firm*—Scott B. Garrison

(57) ABSTRACT

The invention relates to an apparatus for measuring the relative difficulty in donning of a glove. The apparatus contains a glove mount for holding a glove to be tested in an open donnable position and a device for measuring the effort associated with donning the glove. The invention also relates to a method for measuring the effort associated with donning a glove by providing a testing apparatus having a glove mount and a device for measuring effort associated with donning of a glove, mounting a glove for testing on the glove mount so the glove is open and donnable, initializing the testing apparatus, and acquiring data from the device relating to the effort associated with donning of the glove.

25 Claims, 5 Drawing Sheets

APPARATUS FOR MEASURING THE RELATIVE DIFFICULTY IN DONNING A GLOVE

BACKGROUND

The present invention relates to an apparatus and method for measuring the relative difficulty in donning a glove. More particularly, the apparatus provides quantitative data with respect to the donning of gloves typically used in environments such as surgical arenas, examination rooms, emergency medical services, and clean rooms.

During the preparation for surgery, surgeons and nurses will typically scrub, dry, and then, don surgical gloves. On many occasions, the subject's hands may not be completely dry, but damp. This dampness on the hands can impede the donning of the surgical glove and is referred to as damp donning.

Surgical gloves must be form fitting and tight around the hands to be effective. The tight fit and rubbery composition make it difficult to don the gloves without a lubricant. Traditionally, surgical gloves are dusted with a dry powder lubricant such as cornstarch in order to facilitate the glove donning process. However, in surgical settings it is believed that the microscopic starch granules can contaminate the body cavity and exacerbate the formation of adhesions. This is a compelling reason to eliminate the use of powder in surgical gloves by modifying the inside or donning surface of the glove with a liquid or gelatinous lubricant. Such powder free gloves typically do not don as well as powdered gloves. As such, the development of a powder-free glove with excellent donning properties is a high priority for the surgical community.

The overall force, time and energy used to don a glove can be defined as the "donning effort". The sole purpose of a lubricant is to reduce the overall effort required to don the glove. An extensive amount of research has been performed using both human subjects and various other surfaces in an attempt to understand how coefficient of friction (COF) correlates to glove donning. Due to various factors, the studies conducted have not provided conclusive results. This is partly because there has not been an apparatus capable of accurately measuring the donning characteristics of gloves and how donning ultimately correlates to end-users.

An apparatus capable of generating quantitative data in this area may lead to methods capable of distinguishing donning characteristics between different gloves. Additionally, such data may lead to the development of methods useful for in-process testing during glove production.

Therefore what is needed is an apparatus and method capable of measuring the relative difficulty in donning a glove, including acquiring and quantifying data on the effort associated with donning the glove.

SUMMARY OF THE INVENTION

As such, one aspect of the present invention discloses an apparatus for measuring the relative difficulty in donning of a glove. Such an apparatus contains a glove mount that is adapted to hold a glove in an open donnable position and a device for measuring the effort associated with donning the glove.

Another aspect of the present invention discloses an apparatus for measuring the relative difficulty in donning of a glove having a base and a device for acquiring data on the effort associated with donning the glove. A glove mount is slidably engaged with the base. The glove mount is adapted to hold the glove in an open donnable position.

Another aspect of the present invention configures the glove mount as a moveable arm assembly terminating in a glove seat upon which the glove is mounted and held in the open donnable position.

Yet another aspect of the present invention provides a method for measuring the effort associated with donning a glove. A testing apparatus having a glove mount and a device for measuring the effort associated with donning of a glove is provided. A glove for testing is mounted on the glove mount so the glove is open and donnable. The testing apparatus is initialized and data from the device relating to the effort associated with donning of the glove is collected.

Still another aspect of the present invention contemplates a method for measuring the effort associated with donning a glove in which a testing apparatus having a glove mount and a device for measuring effort associated with donning of a glove is provided. A glove is stretched onto the glove mount so that the glove is presented to a test subject in an open and donnable arrangement. The testing apparatus is initialized and a test subject's hand is prepared for glove donning. As the glove is donned the device acquires data relating to the effort associated with donning of the glove.

DESCRIPTION OF THE INVENTION

Figure 1:
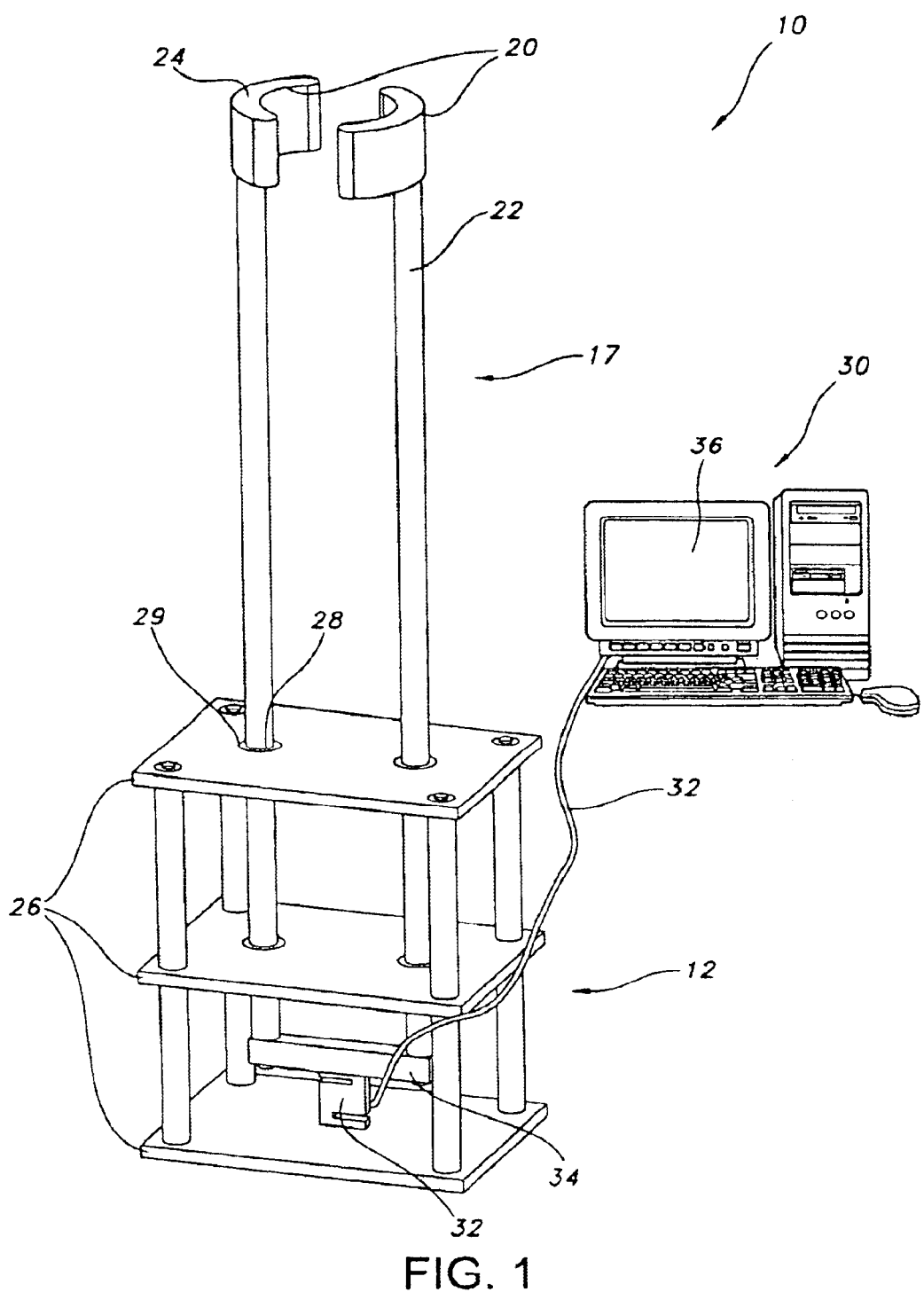
FIG. 1 depicts an embodiment of an apparatus for measuring the relative difficulty in donning a glove in accordance with one aspect of the present invention.

The present invention and its advantages are best understood by referring to the drawings, like numerals being used for like and corresponding parts of the various drawings. Looking first to FIG. 1, an apparatus for quantitatively measuring the relative difficulty in donning of a glove is labeled as reference numeral 10.

In one embodiment, the apparatus 10 may be configured as a two part structure including a base assembly or base 12 and a glove mounting assembly or glove mount 17. Other possible embodiments contemplate the apparatus 10 as comprising a glove mount 17 independent of a base 12. Such an embodiment (not shown) may be suitable for mounting to a preexisting structure or surface such as a table or wall.

Figure 2:
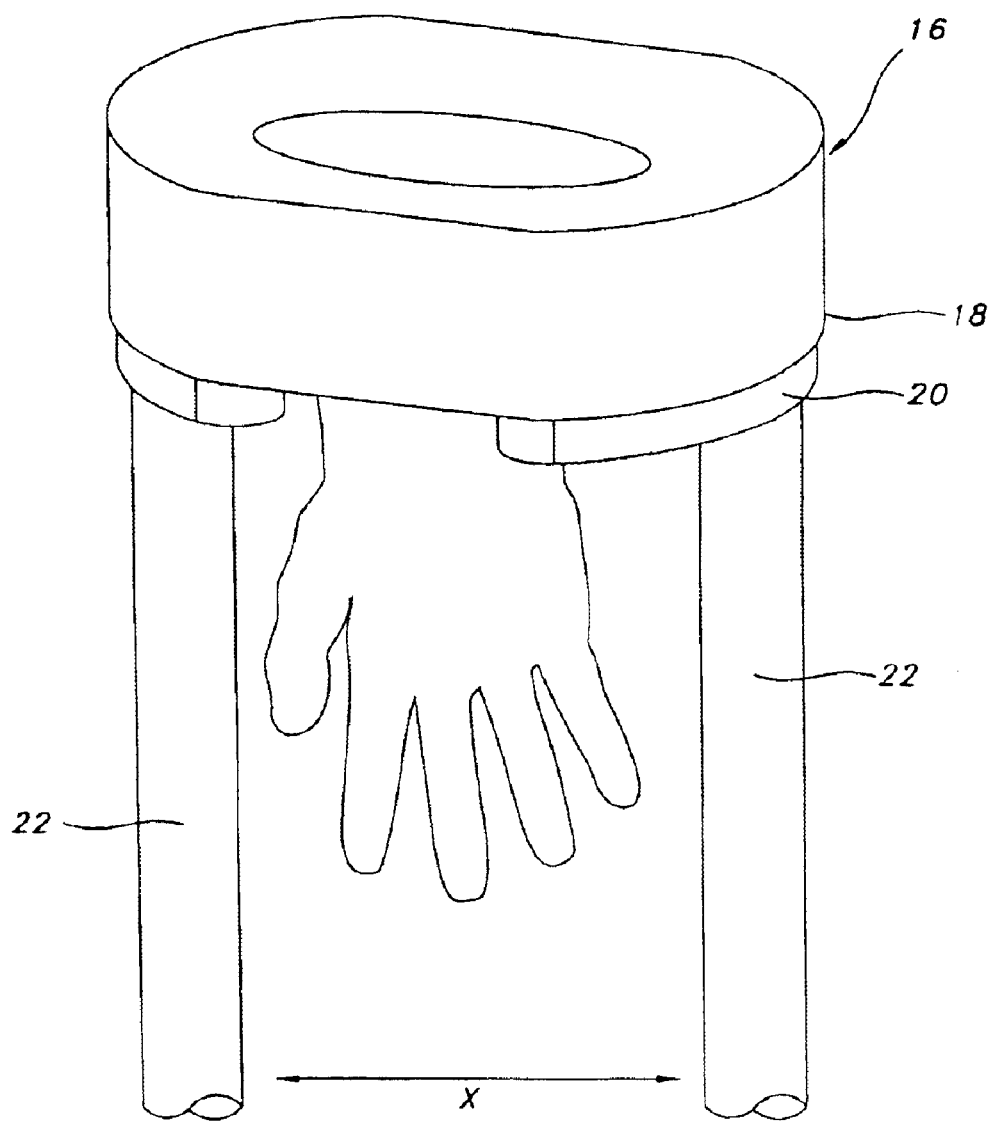
FIG. 2 depicts a detailed view of one embodiment of the arms and glove seats of the FIG. 1 apparatus.

Looking now to FIG. 2, a glove 16 to be tested is secured in or on the apparatus 10 in an open donnable position. A number of configurations are possible with respect to methods for securing or otherwise mounting the glove in or on the apparatus 10 so that it is open and donnable. As shown in FIG. 2, the glove 16 may be held on the glove mount 17 by stretching the glove 16 at its cuff 18 over a pair of opposed glove seats 20 so that the friction between the glove seat and the glove holds the glove in place. The opposed glove seats 20 in this embodiment may be affixed to or otherwise formed upon arms 22.

In any event, the apparatus 10 is designed to enable a test subject to thrust his hand into the open glove 16 between the arms 22 thus donning the glove. To facilitate this process, the glove seats 20 may oppose one another as shown in FIGS. 1 and 2. This configuration has been found to more accurately duplicate glove donning conditions typically encountered in the surgical arena.

By way of explanation, in the surgical arena commonly a surgeon is assisted in donning surgical gloves. The typical practice is for a nurse, technician, or other assistant to hold an individual glove open with both hands in front of the surgeon by grasping the glove cuff on opposing sides and pulling the glove open. Usually the glove is opened laterally, i.e., substantially along the plane generally defined by a person's open and flattened hand. The surgeon, faced with the open glove thrusts his hand into the glove as quickly and firmly as possible in order to don the glove in a single fluidic motion with the expectation that he will minimize the repositioning of the glove on the hand to secure a proper fit. Once the first glove is donned, the surgeon may assist the assistant with the donning of the second glove by grasping the glove cuff between the assistant's hands and pulling the glove open in a manner similar to that of the assistant. The procedure, with or without the surgeon's assistance is commonly referred to as assisted donning and is well understood by those in the field.

In some aspects, the present invention is designed to simulate this process of assisted donning. Until now, no other apparatus has been found to accurately imitate the process under laboratory conditions while providing useable data on the donning process itself. Looking to FIGS. 1 and 2, it is apparent that the glove seats 20 may be arcuately shaped and oriented so that concave portions of each glove seat 20 generally face one another. The area formed by a first surface 24 of each glove seat 20 may in some embodiments be sized to approximate the area formed by the tips of an assistant's fingers. For example, in some embodiments the total length of each first surface 24 may range from about one (1) inch to about three (3) inches. However, areas greater than this are contemplated as well.

Figure 3:
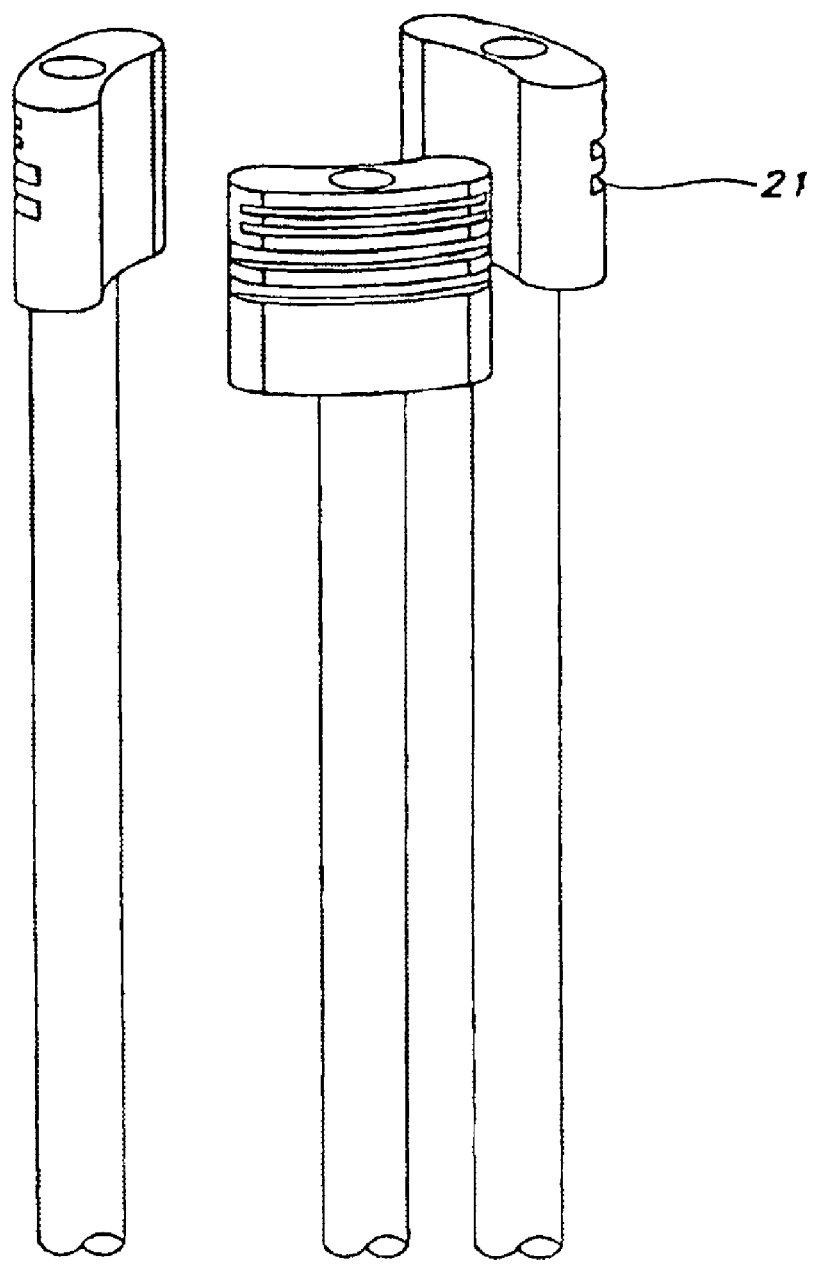
FIG. 3 depicts another alternate embodiment of the FIG. 1 apparatus in accordance with the present invention.

Moreover, in some embodiments, such as that shown in FIG. 3 a third glove seat 20 may be added to more accurately simulate those conditions in which the surgeon assists in donning the glove. In the embodiment illustrated, it may be seen that the glove seats 20 are arranged in a circular pattern with the concave portions of the glove seats facing a common center point. It should be noted that the glove seats are not required to be arranged in a circular pattern, other arrangements that allow the glove to be held in open and donnable position are contemplated as well. One such variation may comprise a triangular arrangement (not shown).

Moreover, though the glove seats 20 may be smooth as shown in FIG. 1, FIG. 3 illustrates that the glove seats 20 may also be knurled, ribbed, coated, striated, grooved, ridged or provided with some other form of surface texture to increase the coefficient of friction between the glove cuff 18 and the seat 20. For example, FIG. 3 depicts grooves 21. As indicated, numerous other arrangements are possible with respect to the shape, size, number, orientation, and arrangement of the glove seats. In one possible embodiment the individual glove seats 20 may be replaced by a ring or partial ring (not shown). Regardless of the specific configuration or configurations selected, it is important that the apparatus 10 be provided with some manner or mechanism to hold the glove 16 in an open and donnable position as shown in FIG. 2 without tearing the glove during the testing procedure.

In like manner, the quantity, orientation, and shape of the arms 22 themselves can vary. However, their configuration must accommodate a person's hand in such a way that the glove 16 held in the apparatus 10 can be donned and removed without the test subject impacting the glove seats 20 or any other part of the apparatus 10 inadvertently. For example, the arms 22 may be made adjustable in a number of possible embodiments. In one embodiment, the linear distance between each arm 22 may be adjustable as symbolized by the arrow "x" in FIG. 2. This feature could prove useful in that it may allow different size gloves to be mounted upon the glove seats 20 under optimal testing conditions. Moreover, the adjustability would more easily accommodate different hand sizes as well.

Figure 4:
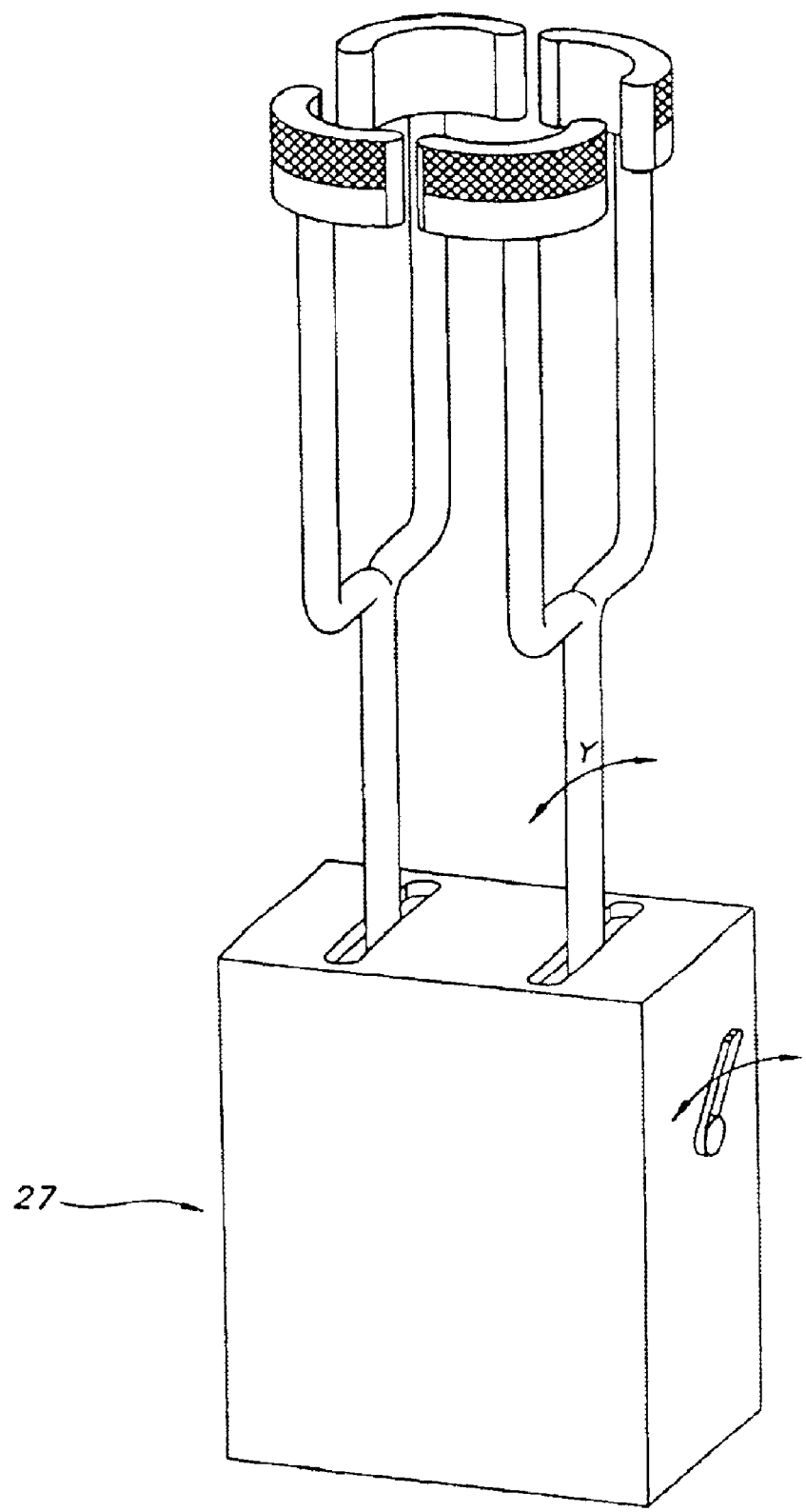
FIG. 4 depicts yet another alternate embodiment of the FIG. 1 apparatus in accordance with the present invention.

Another useful embodiment contemplates providing the arms or the entire apparatus with the ability to tilt or pivot about at least one axis. This is depicted in FIG. 4. The ability to tilt enables the opened glove to be oriented in a way best suited to the test subject for donning. In other words, one person may find it more natural to don the glove in a vertically downward fashion whereas another person may find it more natural to have the glove 16 presented for donning at an orientation, for example, somewhere between vertical and horizontal. Providing the apparatus 10 with means to tilt or otherwise customize the presentation of the glove at an optimal donning orientation with respect to the test subject may be regarded as a beneficial feature. Such a feature and the manner in which it is incorporated into the apparatus would be well known and understood in the art.

Figure 5:
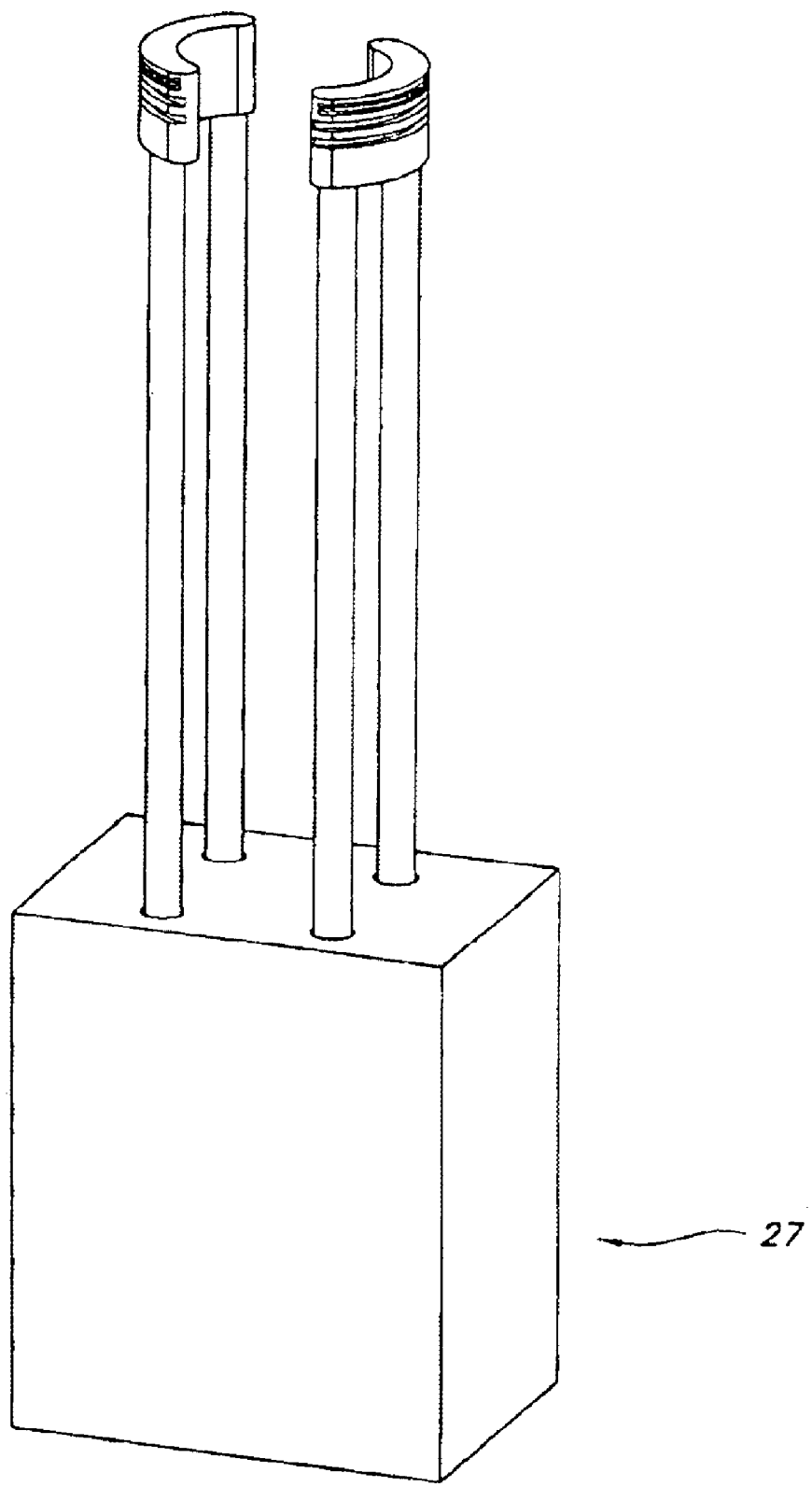
FIG. 5 depicts another alternative arm arrangement of the apparatus.

As previously discussed, the number of glove seats 20 of the apparatus 10 may vary, likewise the quantity and construction of the arms 22 may vary as well. The FIGS. 1 and 2 embodiments depict two arms 22 each having an independent glove seat 20. The FIG. 3 embodiment depicts a three arm arrangement. Another embodiment may be provided by a single arm 22 for accommodating two or more glove seats 20. Two configurations of this embodiment selected from many other possibilities are to manufacture each arm in a "Y" configuration or the "squared-Y" configuration as shown in FIG. 4. Though FIG. 4 depicts a double arm arrangement, a single arm similar to the FIG. 4 embodiment may terminate in two glove seats configured similar to the FIG. 2 embodiment. Another possible embodiment contemplates that each glove seat 20 is affixed to or otherwise associated with two or more arms such as shown in FIG. 5. Other possible arrangements are contemplated, including further single arm configurations, two arm configurations, and three or more arm configurations.

The base assembly or base 12 itself serves as a support structure for the glove mount 17. Therefore its configuration is not crucial. Looking back to FIG. 1, the base 12 may be formed from a series of plates 26 arranged to hold the arms 22 in a generally upright position. Of course since the base 12 serves mainly as a support structure for the glove mount assembly 17, it may be configured in any number of other possible ways. For instance, the base may be constructed as an enclosed or semi-enclosed cabinet 27 as shown in FIGS. 4 and 5 which may provide the advantage of enabling a manufacturer to accommodate various measuring devices within the cabinet 27.

In many embodiments of the apparatus 10, the arms 22 should be free to move with respect to the base 12 so that the relative difficulty required to don a given glove can be measured. In one example, referring once again to the FIG. 1 embodiment, it is shown that the arms 22 are slidably engaged with the plates 26 of the base 12 through suitable holes or openings 28 within the plates 26. Friction between the arms 22 and the openings 28 should be minimized or otherwise accounted for in order to more accurately measure the effort needed to don the glove. Bushings 29 made of a material possessing a low coefficient of friction may be placed in the openings 28 to further minimize friction between the arms 22 and the openings 28. Another possibility for reducing friction would be to incorporate bearings (not shown) between moving parts of the apparatus 10.

To actually measure the relative difficulty associated with glove donning, a number of different measuring devices may be suitable. The specific devices chosen may be placed in communication with data collection equipment 30, one possible example comprising a computer system, such as a personal computer. In some embodiments, the data collection equipment 30 may be used to compile data received from the measuring device and record it. For example, in the FIG. 1 embodiment, a load cell 32 is used as the measuring device to directly measure force on the glove as the glove is donned. The load cell 32 may be disposed between the base 12 and an end 34 of the arm or arms 22 opposite the glove seats 20 so that as the glove is donned the forces are transmitted through the arms 22 via the glove seats 20, measured by the load cell 32, and compiled by the data collection equipment 30.

Another embodiment of the measuring device contemplates providing a scale (not shown) to measure the maximum force encountered during donning. One example of such a scale comprises coupling a linear variable differential transducer (LVDT) between the glove mount 17 and a stationary reference such as the base 12. A general description of an LVDT is that the device measures displacement or stretching of the glove between an at rest pre-donned position and a fully distended position which would occur during the donning process. A moveable indicator is placed at the tip of one of the glove fingers when the glove is in the pre-donned position and as the glove is donned the indicator is displaced. The indicator is coupled to a transformer core that is moveable within a magnetic field carried by electrical windings. Movement of the core with respect to the windings correlates to a known displacement. LVDTs are known and those skilled in the art will be familiar with both their operation and use. Though the above moveable indicator was described in use with an LVDT, it should be apparent that such an indicator may be adapted to read directly from a suitable scale. The total displacement may then be read from the scale and correlated mathematically to a measurable donning effort.

Other embodiments of the apparatus 10 contemplate the use of other measuring devices, such as a light curtain or light screen to quantify the effort needed to don the given glove. In general terms, a light curtain is a photoelectric sensor that detects the presence of an object interrupting at least one beam of light in a multi-beam light transmitted between an emitter and receiver pair. As the glove is distended during the donning event, suitable electronic components detect the individual light beams that have been interrupted and correlate this information to, for example, glove displacement. A light curtain may be more advantageous than some of the other measuring devices since it requires no physical contact between the glove and the measuring device other than a means for securing the glove to the glove mount 17. It should be noted that other devices may also be used to obtain data concerning the relative difficulty in donning a glove. For example measuring devices to measure strain, stress, displacement, pressure, work, energy, and/or force, alone or in any combination may be used.

Moreover, the data collection equipment 30 may be configured to perform a number of separate functions. One potential application for the data collection equipment 30 is to use it for data acquisition alone, whereas another application contemplates both data review and analysis, or for example data acquisition, storage, and analysis. A suitable display 36 for viewing the data or the results generated from the data may be provided as well. Such a display may be configured to display the data, results, or both in tabulated form and/or graphical form.

One possible embodiment of the apparatus 10 enables an operator to collect user input information to be associated with a specific glove test. For example, the data collection equipment 30 may prompt the test subject to input such data as the test subject's name, hand size, hand tested, general comments, and a file name under which to store the information and data generated. In some embodiments, it may be convenient to save such data as the default setting for the next test to facilitate data entry on a subsequent test.

In operation, the measuring device may be initialized or zeroed and the display updated or refreshed as appropriate. At this time, the test subject may be prompted to insert a hand in the glove 16. Data acquisition should begin once a sustained, positive load is detected. In one embodiment, approximately five data points per second are acquired and stored. This data may be stored in a two-dimensional array along with the total elapsed time. In certain embodiments acquisition of data should proceed until a predetermined repeat reading is detected, for example, repeat readings below 100 grams may be sufficient.

Alternatively, data acquisition may end after some predetermined period of time has elapsed or until a specific key is pressed on the data collection equipment 30. Once data acquisition has ended both the input information and the two-dimensional data array may be saved as a single file in a series of sequential tests. The test subject may then be prompted to start another test or quit. A tabulated and/or graphical depiction of the data may then be displayed on the display for analysis and review. Information such as peak load, total linear displacement of the glove, the area under the load curve, etc. may be calculated and displayed as well.

Another aspect of the present invention pertains to a method for measuring the relative difficulty in donning a glove. An example of a suitable procedure requires preparation of the test subject and the apparatus prior to the test being conducted. In one method, the test subject is first asked to remove all jewelry from the wrists and hands. The fingernails should be checked to ensure that they are sufficiently manicured to minimize the potential that the fingernails might tear the glove. If necessary, the fingernails should be trimmed. As soon as the apparatus itself is prepared, the test may begin.

In the event that the test is designed to simulate damp donning conditions, additional test subject preparations are necessary. One possible method contemplated to simulate damp donning calls for the test subject's hands to be washed thoroughly with soap and warm water for a specified period of time, for example 15 seconds. The test subject's hands should be washed up to approximately the mid arm, that is, to a region approximately five inches up from the wrists. The washing should be done vigorously to ensure that all parts are appropriately scrubbed and lathered to more accurately simulate conditions encountered in the medical field. Once the test subject's hands are adequately cleaned the hands are rinsed for a comparable period of time, e.g., 15 seconds. The hands are next dried with a towel until all visible moisture is removed from the skin. At this point, to simulate damp donning, the glove should be immediately donned. Should the test subject perform a series of glove donning events, it may be adequate to skip the washing step and simply rinse and dry the hand as described.

As stated above, the apparatus itself also requires preparation, which may or may not precede the preparation of the test subject. In one method, the glove 16 is mounted on the apparatus 10 and oriented in a predetermined direction. Indicia may be placed on the apparatus to assist in identifying the proper orientation of the glove. The glove cuff 18 is affixed to the glove mounts 17 so that the middle fingertip of the glove 16 hangs between the arms 22 a predetermined distance from the surfaces 24 of the mounts 17.

After all preparations have been completed, the test subject may partially insert his fingertips into the openings for the corresponding glove fingers. During this positioning phase a light flexing of the fingers and hand on the part of the test subject is acceptable. The finger tips and thumb should be aligned taking precaution that the thumb is also aligned with the glove properly. The test subject should lift his hand slightly to eliminate any force from registering on the measuring device. Alternatively the test subject may align his fingers in a similar manner above the glove so that no contact occurs prior to the donning. In either event, at this time the measuring device should be initialized.

The test subject next plunges his hand in one smooth action into the glove 16 and in some embodiments withdraws his hand in a similar smooth action once the glove is fully donned. In most instances, the donning and extraction of the hand should be done in one fluid, non-stop motion. The data collection equipment 30 in conjunction with the display 36 may be used to assemble and display the data in the desired fashion for use by the test subject.

EXAMPLE

A series of tests were conducted with the apparatus 10. Sixteen female subjects participated in this study. Each of the test subjects' hands were screened for any skin deviations and sized to ensure that they wore a glove size between size 6.5 and 7 prior to receiving training.

Each test subject evaluated six different gloves, more specifically two different sizes, a size 6.5 and a size 7 glove from three different manufacturers. Each test subject received a new sample of each of the glove sizes from each of the same manufacturers. Each glove tested came from the same glove lot to minimize the potential variability in gloves from different lots. The order in which each test subject tested her specific gloves was random.

The apparatus 10 was configured similar to that depicted in FIG. 1. Load cell 32 was used as the measuring device. Specifically a 10,000 gram Dillon Quantrol™ smart load cell was used. This particular load cell has an S-configuration shape approximately 2.0 inches long by 0.5 inches wide by 2.5 inches tall. A Dillon Quantrol™ Advanced Force Gauge was used to collect data on peak force measurement.

The test subjects arrived and were briefed on the objective of the study and asked to practice on two to four gloves prior to beginning the evaluation. A surgical glove 16 was placed on the glove seats 20. Each test subject was asked to wash and dry her hands according to the above hand preparation protocol. After removing all visual signs of water from her hands each subject aligned her fingertips into the fingers of the glove as described above. The apparatus 10 was reset and each subject plunged her hand into the glove using a downward even force. The maximum value in grams was recorded on a spreadsheet.

Additionally, after donning each glove, each test subject was asked to rate the donning of each glove subjectively using the following 1 to 5 Sensory Panel rating scale:

5—Excellent Easy to slide on, no adjustment required

4—Good Donning Glove seats on the hand and fingers. Minimal adjustment required.

3—Fair Donning Can get the glove on the hand, with reasonable fit. Fingers bottom out, minimal webbing in finger crotches. Takes more effort and time to get on and more glove adjustment required than a "4-Good Donning" glove.

2—Poor Donning Can get the glove most of the way on the hand, but it takes significant time and effort. Excessive webbing in finger crotches and fingers won't seat.

1—Failed Donning Can not get the glove on the hand, fingers won't insert, nearly full fingers undonned. Absolute failure.

The data from these tests have been compiled in Table I below. The test subjects have been identified as Subject 1 through 16. It should be noted that each Subject has two lines of test data attributed to her. This correlates to the two sizes of gloves tested from each of the three manufacturers. Adjacent to each test result is the test subject's subjective rating of glove donning characteristics in accordance with the above sensory panel rating system. The test results for both gloves from each manufacturer were averaged together. In looking at these averages, a strong correlation can be seen between the empirical data obtained from the test apparatus and the subjective testing.

TABLE I

| SUB-JECT | MANUFACTURER 1 | | MANUFACTURER 2 | | MANUFACTURER 3 | |
|---|---|---|---|---|---|---|
| | Test with Apparatus (grams) | Sensory Panel Rating | Test with Apparatus (grams) | Sensory Panel Rating | Test with Apparatus (grams) | Sensory Panel Rating |
| 1 | 2858 | — | 5626 | — | 4736 | — |
| 1 | 2608 | — | 10000 | — | 6682 | — |
| 2 | 2966 | 5 | 10000 | 1 | 2554 | 4 |
| 2 | 3032 | 4 | 6336 | 4 | 2384 | 5 |
| 3 | 7234 | 5 | 6412 | 1 | 4864 | 5 |
| 3 | 7116 | 4 | 10000 | 1 | 4452 | 5 |
| 4 | 4512 | 5 | 6892 | 1 | 4060 | 5 |
| 4 | 4206 | 5 | 5938 | 1 | 4398 | 5 |
| 5 | 4130 | 1 | 5612 | 1 | 4948 | 4 |
| 5 | 6246 | 4 | 6348 | 1 | 6190 | 5 |
| 6 | 6000 | 5 | 6184 | 1 | 4388 | 4 |
| 6 | 3640 | 5 | 6884 | 1 | 5394 | 4 |
| 7 | 7312 | 3 | 10000 | 1 | 3626 | 4 |
| 7 | 5462 | 5 | 7544 | 1 | 5478 | 5 |
| 8 | 2832 | 5 | 6356 | 3 | 2614 | 5 |
| 8 | 5772 | 5 | 6898 | 2 | 2436 | 5 |
| 9 | 4142 | 4 | 7884 | 1 | 2560 | 5 |
| 9 | 4023 | 4 | 10000 | 1 | 3730 | 5 |
| 10 | 3906 | 5 | 5130 | 1 | 3648 | 5 |
| 10 | 3204 | 5 | 5480 | 1 | 4534 | 4 |
| 11 | 4278 | 4 | 10000 | 1 | 3984 | 5 |
| 11 | 4048 | 4 | 4828 | 2 | 3186 | 5 |
| 12 | 3936 | 5 | 5520 | 1 | 5874 | 4 |
| 12 | 5284 | 5 | 6614 | 1 | 4204 | 4 |
| 13 | 4584 | 5 | 5466 | 2 | 4692 | 3 |
| 13 | 6158 | 5 | 6390 | 2 | 5672 | 5 |
| 14 | 3052 | 5 | 5020 | 2 | 3350 | 5 |
| 14 | 2928 | 5 | 4924 | 4 | 3702 | 5 |
| 15 | 4434 | 4 | 3970 | 1 | 3502 | 1 |
| 15 | 4816 | 5 | 5168 | 1 | 4840 | 5 |

TABLE I-continued

| SUB-JECT | MANUFACTURER 1 | | MANUFACTURER 2 | | MANUFACTURER 3 | |
|---|---|---|---|---|---|---|
| | Test with Apparatus (grams) | Sensory Panel Rating | Test with Apparatus (grams) | Sensory Panel Rating | Test with Apparatus (grams) | Sensory Panel Rating |
| 16 | 3454 | 5 | 6820 | 2 | 2680 | 5 |
| 16 | 2422 | 5 | 4634 | 1 | 2190 | 5 |
| avg | 4393.6 | 4.53 | 6714.9 | 1.47 | 4111.0 | 4.53 |
| st dev | 1398.7 | 0.86 | 1811.6 | 0.86 | 1193.6 | 0.86 |

While the invention has been described in detail with respect to specific preferred embodiments thereof, it will be appreciated that those skilled in the art, upon attaining an understanding of the foregoing, may readily conceive of alterations to and variations of the preferred embodiments. Such alterations and variations are believed to fall within the scope and spirit of the invention and the appended claims.

What is claimed is:

1. An apparatus for measuring the relative difficulty in donning of a glove comprising:
    a glove mount adapted to hold a glove in an open donnable position, the glove mount moveable with respect to a fixed reference, wherein the glove mount comprises two opposed arms connected to one another at a first end of each and terminating at a second end of each in at least one glove seat; and
    a device for measuring the effort associated with donning the glove.

2. The apparatus of claim 1 wherein the fixed reference comprises a base.

3. The apparatus of claim 1 wherein the device comprises a load cell disposed between the glove mount and the fixed reference.

4. The apparatus of claim 1 wherein the device collects data on the force exerted between the glove mount and the fixed reference while the glove is being donned.

5. The apparatus of claim 1 wherein the device collects data on any of: a force exerted between the glove mount and the fixed reference, linear movement of the glove with respect to the fixed reference, linear movement of the glove mount with respect to the fixed reference, and peak load registered on the glove.

6. The apparatus of claim 1 wherein the at least one glove seat is arcuately shaped.

7. The apparatus of claim 1 wherein the at least one glove seat is annular.

8. The apparatus of claim 1 wherein the at least one glove seat is about one inch to about three inches in length.

9. The apparatus of claim 1 wherein the at least one glove seat comprises a textured surface.

10. The apparatus of claim 1 wherein the at least one glove seat is any of coated, knurled, ribbed, ridged, striated, and grooved.

11. The apparatus of claim 1 comprising two glove mounts disposed in spaced-apart, opposed relation with respect to the other forming a throat therebetween.

12. The apparatus of claim 1 wherein at least one glove seat on each arm is in opposed relation to at least one glove seat on the other arm.

13. The apparatus of claim 1 wherein the arms are manipulable in at least one of: their distance from one another, and their orientation with respect to the fixed reference.

14. The apparatus of claim 1 wherein the glove mount is pivotable with respect to the fixed reference.

15. An apparatus for measuring the relative difficulty in donning of a glove comprising:
    a base;
    a glove mount slidably engaged with the base adapted to hold a glove in an open donnable position, wherein the glove mount comprises at least two interconnected arms, each arm being spaced from the other a distance, interconnected at a first end, and each arm terminating at a second end in a glove seat suitable for mounting the glove thereon and holding the glove in the open donnable position; and
    a device for acquiring data on the effort associated with donning the glove.

16. The apparatus of claim 15 wherein the device comprises a load cell disposed between the glove mount and the base.

17. The apparatus of claim 15 wherein each glove seat is arcuately shaped.

18. The apparatus of claim 15 wherein the glove seats are interconnected to form a ring through which the glove is donned.

19. The apparatus of claim 15 wherein each glove seat is about one inch to about three inches in length.

20. The apparatus of claim 15 wherein the glove seats comprise a textured surface.

21. The apparatus of claim 15 wherein the glove seats are coated to increase their coefficient of friction.

22. The apparatus of claim 15 wherein the distance separating the arms is adjustable.

23. The apparatus of claim 15 wherein the arms are pivotable with respect to the base.

24. The apparatus of claim 15 wherein the glove mount is pivotable with respect to the base.

25. An apparatus for measuring the relative difficulty in donning of a glove comprising:
    a base;
    a glove mount slidably engaged with the base, the glove mount comprising a moveable arm assembly terminating in a glove seat at a first end suitable for mounting the glove thereon and holding the glove in the open donnable position and
    a device for acquiring data on the effort associated with donning the glove.

* * * * *